United States Patent
Bayer et al.

(10) Patent No.: US 8,741,073 B2
(45) Date of Patent: *Jun. 3, 2014

(54) IMPLANT AND METHOD FOR PRODUCING THE SAME

(75) Inventors: Ullrich Bayer, Admannshagen-Bargeshagen (DE); Alexander Rzany, Nuremberg (DE)

(73) Assignee: Biotronik AG, Buelach (CH)

( * ) Notice: Subject to any disclaimer, the term of this patent is extended or adjusted under 35 U.S.C. 154(b) by 201 days.

This patent is subject to a terminal disclaimer.

(21) Appl. No.: 13/164,082

(22) Filed: Jun. 20, 2011

(65) Prior Publication Data

US 2011/0319986 A1 Dec. 29, 2011

Related U.S. Application Data

(60) Provisional application No. 61/359,365, filed on Jun. 29, 2010.

(51) Int. Cl.
*C23C 8/36* (2006.01)

(52) U.S. Cl.
USPC .......................................... 148/239; 148/525

(58) Field of Classification Search
CPC .................................. A61F 2/82; C23C 8/36
USPC ................................................. 148/525, 239
See application file for complete search history.

(56) References Cited

U.S. PATENT DOCUMENTS

| | | | |
|---|---|---|---|
| 8,337,936 B2 * | 12/2012 | Bayer et al. | 427/2.1 |
| 2003/0188972 A1 * | 10/2003 | Shatrov et al. | 205/91 |
| 2003/0213771 A1 * | 11/2003 | Ohshita et al. | 216/83 |
| 2004/0053058 A1 * | 3/2004 | Kamitani et al. | 428/429 |
| 2005/0079088 A1 * | 4/2005 | Wirth et al. | 420/402 |
| 2010/0210745 A1 * | 8/2010 | McDaniel et al. | 521/55 |
| 2012/0053679 A1 * | 3/2012 | Fircho et al. | 623/1.46 |

* cited by examiner

*Primary Examiner* — Jie Yang
(74) *Attorney, Agent, or Firm* — Biotech Beach Law Group, PC

(57) ABSTRACT

A method for producing an implant, particularly an intraluminal endoprosthesis, having a body, wherein the body comprises magnesium or a magnesium alloy. In order to control the degradation in a desired time window, such as between four weeks and six months, the following production method is carried out: a) preparing the implant body, b) applying a metallic coating onto at least a portion of the body surface, the primary constituent of the coating being at least one element of the group containing titanium and aluminum, c) plasmachemical treatment of the portion of the body surface provided with the coating in an aqueous solution in order to produce a layer created by plasmachemical treatment by applying a mixed voltage generating the plasma to the body of the implant, wherein the mixed voltage has sufficient energy to temporarily ionize both the metallic coating and a subjacent region of the implant body. The invention further relates to an implant that can be obtained by such a method.

12 Claims, 2 Drawing Sheets

IMPLANT AND METHOD FOR PRODUCING THE SAME

CROSS REFERENCE TO RELATED APPLICATIONS

This invention claims benefit of priority to U.S. patent application Ser. No. 61/359,365, filed on Jun. 29, 2010; the contents of which are herein incorporated by reference in their entirety.

TECHNICAL FIELD

The invention relates to a method for producing an implant, particularly an intraluminal endoprosthesis, having a body, wherein the body comprises magnesium or a magnesium alloy, and to an implant that can be obtained or is obtained by such a method.

BACKGROUND

Medical endoprosthesis or implants for a wide variety of applications are known from the state of the art in great diversity. Implants as defined by the present invention are endovascular prostheses or other endoprostheses, for example stents, fastening elements for bones, such as screws, plates or nails, surgical suture material, intestinal clamps, vascular clips, prostheses in the area of hard and soft tissues, such as anchoring elements for electrodes, particularly for pacemakers or defibrillators.

These days, stents that are used for the treatment of stenoses (vascular constrictions) are employed especially frequently as implants. They have a body in the form of a tubular or hollow-cylindrical base mesh, which is open at both longitudinal ends. The tubular base mesh of such an endoprosthesis is inserted into the vessel requiring treatment and is intended to support the vessel. Stents have become established in particular for the treatment of vascular diseases. Constricted areas in the vessels can be dilated through the use of stents, resulting in increased lumen. While through the use of stents or other implants, an optimal vascular cross-section can be achieved, which is primarily necessary for successful treatment, the lasting presence of such a foreign object triggers a cascade of microbiological processes, which may result in gradual blockage of the stent and, in the worst case, in vascular obliteration.

One approach to solve this problem is to produce the stent or other implants from a biodegradable material.

Biodegradation refers to hydrolytic, enzymatic and other metabolic decomposition processes in the living organism, which are caused primarily by the body fluids coming in contact with the biodegradable material of the implant and result in a gradual dissolution of the structures of the implant containing the biodegradable material. This process causes the implant to lose the mechanical integrity thereof at some point. A term that is frequently used synonymously with biodegradation is biocorrosion. The term bioresorption encompasses the subsequent resorption of the decomposition products by the living organism.

Materials that are suitable for the body of biodegradable implants may comprise polymers or metals, for example. The body can be produced from several of these materials. The common characteristic of these materials is the biodegradability thereof. Examples of suitable polymer compounds include polymers from the group consisting of cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyorthoesters, polyethylene terephtalate (PET), polymalonic acid (PML), polyanhydrides, polyphosphazenes, polyamino acids and the copolymers thereof, as well as hyaluronic acid. Depending on the desired properties, the polymers may be present in pure form, in derivatized form, in the form of blends or as copolymers. The present invention relates to implants comprising a metallic biodegradable material that is based on magnesium or magnesium alloys.

Stents comprising coatings that have various functions are already known. Such coatings are used, for example, to release medication, to arrange an X-ray marker, or to protect the subjacent structures.

In the implementation of biodegradable implants, the degradability is to be controlled in accordance with the desired therapy and/or use of the respective implant (coronary, intracranial, renal, etc.). For many therapeutic applications, for example, an important target corridor is that the implant loses the integrity thereof within a period of four weeks to six months. Integrity, that is mechanical integrity, shall be understood as the property whereby the implant suffers hardly any mechanical losses in comparison with the non-degraded implant. This means that the implant still has enough mechanical stability that the collapse pressure, for example, has decreased only slightly, that is, to no less than 80% of the nominal value. If the integrity thereof is preserved, the implant can thus still perform the primary function thereof, which is to keep the vessel open. As an alternative, the integrity can be defined in that the implant is still mechanically so stable that it is hardly subject to any geometric changes in the loaded state thereof in the vessel; for example, it does not slump significantly, which is to say, it still has at least 80% of the dilation diameter under load or, in the case of a stent, hardly any of the supporting struts are broken.

Biodegradable magnesium implants, in particular magnesium stents, have proven to be particularly promising for the stated target corridor of degradation, however not only do they lose the mechanical integrity and/or supporting effect thereof too early, the loss of integrity also fluctuates greatly in vitro and in vivo. This means that, in the case of magnesium stents, the collapse pressure declines too rapidly over time and/or the reduction in the collapse pressure exhibits excessive variability and therefore cannot be sufficiently determined.

Various mechanisms of controlling the degradation of magnesium implants have already been described in the prior art. They are based, for example, on organic and inorganic protective layers or combinations thereof, which provide resistance to the human corrosion environment and the corrosion processes taking place there. Existing solutions are characterized in that barrier layer effects are achieved, which are based on a spatial separation, preferably free of defects, between the corrosion medium and the metallic material, in particular the metallic magnesium. The protection from degradation is safeguarded by protective layers having various compositions and by defined geometric distances (diffusion barriers) between the corrosion medium and the magnesium base material. Other solutions are based on alloying constituents of the biodegradable material of the implant body, which influence the corrosion process by displacement of the layer in the electrochemical series. Other solutions in the field of controlled degradation induce predetermined breaking effects by applying physical changes (such as local cross-sectional changes) and/or chemical changes in the stent surface (such as multilayers having different chemical compositions locally). However, the solutions described above usually fail to ensure that the dissolution that occurs as a result of the degradation process, and the resulting breakage of the stents, take place in the required time window. The result is that degradation of the implant begins either too early or too late or the variability in the degradation is excessive.

A further problem encountered in connection with coatings is that stents or other implants usually assume two states, namely a compressed state having a small diameter and an expanded state having a larger diameter. In the compressed state, the implant can be inserted into the blood vessel to be supported by means of a catheter and positioned at the site to be treated. At the site of treatment, the implant is then dilated by means of a balloon catheter, for example. Because of this change in diameter, the body of the implant is exposed to mechanical stress. Additional mechanical stresses on the implant may occur during production or movement of the implant in or with the vessel in which the implant is inserted. With the known coatings, this results in the disadvantage that the coating cracks during the deformation of the implant (such as the formation of microcracks) or is removed in some regions. This may result in an unspecified local degradation. Furthermore, the onset and the speed of the degradation depend on the size and distribution of the microcracks, which form due to deformation and are imperfections that are difficult to monitor. This results in wide variations of the degradation times.

A medical device, such as a catheter or stent, is known from the documents US 2008/0086195 A1 and WO 2008/045184 A1, wherein a polymer-free coating is applied by way of a plasma electrolytic process (plasma electrolytic deposition, PED). The plasma electrolytic coating is used to introduce additional active ingredients containing a medication or a therapeutic agent into the coating. The plasma electrolytic coating comprises plasma electrolytic oxidation (PEO), micro-arc oxidation (MAO), plasma-arc oxidation (PAO), anodic spark oxidation, and plasma electrolytic saturation (PES). The plasma electrolytic coating is carried out by using alternating voltage. The plasma electrolytic treatment includes the use of various electric potentials between the medical device and a counter-electrode, which generates an electric discharge (a spark discharge or a micro-arc plasma micro discharge) at or in the vicinity of the surface of the medical device, which does not bring about any significant extension in the degradation times. The method provided in these publications thus does not solve the problem stated above.

An implant and a method for producing an implant are known from the document DE 10 2008 042 602, wherein a body made of metallic material is subjected to a plasmachemical treatment. Due to the plasmachemical treatment, a layer, which comprises phosphates, hydroxides and oxides of the metallic material, strontium carbonate or strontium phosphate, is generated on the body surface with a frequency of at least 1 kHz. While the plasmachemical treatment generates a protective layer on the surface of the implant, which prevents degradation for a while, it has meanwhile been found that a significant increase in the service life of such an implant cannot be achieved in this way.

SUMMARY

Consequently, the object of the present invention is to provide a method for producing an implant, which allows more precise degradation of the implant in the desired target corridor. The degradation is to take place at a better controllable time. Accordingly, the object of the invention is also to create such an implant.

The above object is achieved by a method comprising the following steps:
a) preparing the implant body,
b) applying a metallic coating onto at least a portion of the body surface, the primary constituent of the coating being at least one element of the group consisting of titanium and aluminum,
c) plasmachemical treatment of the portion of the body surface that has been provided with the coating in an aqueous solution in order to produce a layer created by plasmachemical treatment by applying a mixed voltage generating the plasma to the body of the implant, wherein the mixed voltage has sufficient energy to temporarily ionize both the metallic coating and a subjacent region of the implant body.

In the method according to the invention, first a metallic coating comprising titanium and/or aluminum is applied onto the body surface of the implant body. Subsequently, a plasmachemical treatment is carried out such that both the metallic coating and a subjacent region of the material of the implant body are temporarily ionized. The plasmachemical treatment therefore comprises both the metallic coating and a subjacent layer of the body surface and transforms these layers into a new layer created by plasmachemical treatment.

The body surface is treated in an aqueous electrolyte system (aqueous solution), and the plasmachemical effects develop directly on the surface of the body of the implant. The plasma on the body surface, which is stable for microseconds, generates reaction products which result in the formation of the layer created by plasmachemical treatment on the body surface. Hereinafter, the combination of the transformed metallic coating and the likewise transformed layer of the subjacent body surface is referred to as the layer created by plasmachemical treatment.

The body of the implant comprises at least part of the implant, preferably the majority of the implant, which brings about the mechanical integrity of the implant. The present invention relates in particular to implants in which the material of the body comprises magnesium as the primary constituent and which is preferably biodegradable.

The advantage of the method according to the invention is that, as a result of the plasmachemical treatment on the body surface of the implant, hydroxides, oxides and phosphates of the metals involved, in particular magnesium and the metals present in the previously applied coating, are formed in the layer created by plasmachemical treatment. Furthermore, alloys of the metals mentioned above are produced in this layer. Upon contact with the body fluid, the layer created by plasmachemical treatment constitutes temporary corrosion protection, which causes delayed degradation.

A very crucial advantage of the method according to the invention over the prior art is that both the metallic coating and a subjacent region of the implant body are temporarily ionized by the high energy of the mixed voltage (also referred to as pulsed voltage) generating the plasma. The voltage rises from initially 0 V over a period of approximately 1 µs to a peak voltage, and then drops parabolically within the subsequent 4 µs. The peak voltage is increased from one pulse to another to a maximum value, which is approximately 450 V. As a result of the inertia of the system (electrolyte, electrodes, mechanical inertia of the charge carriers in the electrolyte), however, the voltage does not return to zero after passing the peak voltage, but decreases only to a minimum value. Afterwards, the voltage increases again to the next peak voltage, etc. The plasma generated in this way not only ionizes the metallic coating, but also the implant body material, which is disposed directly beneath the metallic coating, down to a defined depth which is dependent on the specific energy of the mixed voltage. This creates a firm bond between the implant body and the layer created by plasmachemical treatment, which results in high adhesive strength of the layer disposed on the implant body surface. The layer created by plasmachemical treatment, comprising the constituents of the metallic coating, is quasi alloyed into the surface of the implant body. Consequently, no delamination of the layer created by plasmachemical treatment from the implant body takes place, even under high mechanical stress of the implant according to the invention, such as during stent dilation. The degradation thus takes place in a more controlled manner, because no purely metallic surfaces of the implant body material are exposed.

The energy is the product of the cell voltage U, the current I, and the time, or the product of voltage, current density, surface area, and pulse length. For the plasmachemical treatment preferably energy levels in the range of 0.1 Ws to 10 Ws are used, with the range between 0.5 Ws and 5 Ws energy being particularly preferred for magnesium stents. The energy values stated apply in particular to implants having a total surface area in the range of approximately 100 mm².

For example, at an average cell voltage of 300 V (maximum value of the peak voltage is 400 is V), a current density of 1 A/dm²=10 mA/cm², a pulse length of 5 µs with a pulse pause of 1000 µs, and a coating time of 1 minute, the following energetic relationship is obtained:

$$\text{Implant surface of a stent approximately } 100 \text{ mm}^2 = 0.01 \text{ dm}^2 \text{ Coating energy } W =$$
$$U \cdot I \cdot t_{eff-} = 300 \ V \cdot 0.01 \ dm^2 \cdot 0.005 \ A/dm^2 \cdot 60s = 0.9 \ Ws$$

This means that the surface of an implant, such as a stent having a surface of approximately 100 mm², is surface-treated by a plasmachemical treatment with a coating energy of approximately 0.9 watt seconds.

The degradation-inhibiting, layer created by plasmachemical treatment produced by way of the method according to the invention additionally comprises method-related pores. The surface-analytical examinations conducted before and after the degradation tests have shown that the hydroxide formation, which accompanies the plasmachemical treatment, results in locally limited sealing of the pore bottoms.

The sealing of the bore bottoms can be detected, for example, based on the multistage curve of the pH value of the electrolyte in a corrosion test (in artificial plasma, for example). During the first seven days, the pH value rises, in line with expectations, from 7.4 to 8.5 to 8.7. After replacing the media, which was conducted after seven days, the pH value surprisingly increases from 7.4 to only 8.0. This behavior demonstrates a lower chemical activity of the metallic base material (the magnesium in particular) with the corrosive medium. This effect is accompanied by a stop of the cross-sectional diminution of the material of the implant body, which is recorded after only seven days in the metallographic cross-section polish. This effect can be explained, for example, with the fact that hydroxides of the metallic material fill in the pores in the first layer, whereby the contact of the electrolyte to the metallic base material is suppressed. As a result of this self-healing effect, the service life of the implants is considerably increased under body environment conditions.

In addition, the method-related porous structure of the layer created by plasmachemical treatment exhibits high plastic deformability. The microcracks developing during dilation of a stent, for example, are stopped by way of energy accumulation or dissipation in the pores adjacent to the microcracks. This prevents the delamination of the layer created by plasmachemical treatment.

If desired, a further, for example polymer, coating can be applied onto the layer created by plasmachemical treatment, whereby good adhesion of the coating to the layer created by plasmachemical treatment is attained due to the pore structure.

In addition, the pore structure of the layer created by plasmachemical treatment can act as a substance reservoir, such as for pharmaceutically active substances, which can be embedded as nano- or micro-particles, or for substances that can be used as lubricants in order to reduce the friction coefficient in the catheter. Furthermore, bone growth promoting substances, such as calcium phosphates, as well as temporarily acting contrast media or cell growth inhibiting radioactive substances can be embedded in the pore structure.

A "pharmaceutically active substance" (or therapeutically active or effective substance) in the spirit of the invention shall be understood as a plant, animal or synthetic active ingredient (drug) or a hormone, which in a suitable dose is used as a therapeutic agent for influencing states or functions of the body, for substituting active substances produced naturally by the human or animal body, such as insulin, and for eliminating, or rendering harmless, pathogens, tumors, cancer cells or substances foreign to the body. The release of the substance in the surroundings of the implant has a positive effect on the healing process or counteracts pathological changes of the tissue as a result of the surgical procedure, or in oncology is used to render diseased cells harmless.

Such pharmaceutically active substances, for example, have an anti-inflammatory and/or antiproliferative and/or spasmolytic effect, whereby, for example, restenoses, inflammations or (vascular) spasms can be avoided. Such substances may comprise one or more substances of the active ingredient group consisting of the calcium channel blockers, lipid regulators (such as fibrates), immunosuppressants, calcineurin inhibitors (such as tactrolimus), antiphlogistics (such as cortisone or dichlofenac), anti-inflammatory agents (such as imidazoles), anti-allergic drugs, oligonucleotides (such as dODN), estrogens (such as genistein), endothelial forming agents (such as fibrin), steroids, proteins, hormones, insulins, cytostatic drugs, peptides, vasodilators (such as sartanes), and the antiproliferatively acting substances of the taxols or taxanes, preferably paclitaxel or sirolimus.

Additionally, no risk of hydrogen embrittlement exists, due to the anodic mechanism of action of the plasmachemical coating. There is also no risk of mechanical damage because the surface roughening is not performed mechanically.

A further advantage of the method according to the invention is that surface contamination of the base material, which cannot be removed, is absorbed by the layer created by plasmachemical treatment and thus does not additionally influence the degradation process. Moreover, segregations of the implant body protruding from the surface, some of which have sharp edges, (such as undissolved alloying constituents) are covered. This also results in increased hemocompatibilty and/or biocompatibility.

Due to the presence of the layer created by plasmachemical treatment produced by way of the method according to the invention, the storage and transport conditions for implants produced by the method according to the invention are also simplified because the stability of such an implant to degradation is higher than that of uncoated implants.

In a preferred embodiment, a first layer thickness of the metallic coating after completing step b) is approximately 0.1 µm to approximately 3 µm. The stated thickness of the metallic coating is selected such that the entire metallic coating, including the subjacent material of the implant body, can be briefly ionized by using plasmachemical oxidizing plants. In addition, the degradation speed can be controlled by varying the layer thickness. This also opens up the possibility to adapt the degradation duration of the implant to the specific implantation site (coronary, intracranial, renal etc.).

It is furthermore advantageous to apply the metallic coating by way of an ionic fluid.

As an alternative, PVD and CVD methods (such as sputtering or thermal vapor deposition) can be employed to apply the metallic coating. However, when using magnesium as the implant material, these methods must not exceed a temperature of approximately 450° C. and a treatment time of 60 minutes. Otherwise the process would result in irreversible changes to the mechanical material properties (loss of cohesion). Compared to coating by way of ionic fluid, however, coating by way of PVD or CVD methods has the disadvantage that no uniform coverage of the implant surface takes place, which frequently has complicated shapes. These methods are therefore particularly suited for implants that have surfaces with simple shapes.

In contrast, coating by way of ionic fluids can be used for implants having complicated shapes. Such a coating method allows a uniform layer thickness to be achieved, even for complicated shapes (such as on the insides of stents), and therefore significantly contributes to a uniform degradation behavior, following the plasmachemical treatment.

In a further embodiment, the implant is rinsed in a solvent, preferably distilled $H_2O$, after the plasmachemical coating and is then dried, preferably at a temperature of at least about 80° C., particularly preferably at least about 100° C., wherein the drying process is preferably carried out in a circulating air oven. This procedure effects the residue-free removal of compounds of the plasmachemical electrolyte from the implant surface. Drying at elevated temperatures also ensures that electrolyte residue, which may adhere for a longer period due to capillary action (such as in the filigree surface shape of a stent), has no undesirable reactions with the implant surface.

In a preferred embodiment, the aqueous solution comprises $Sr^{2-}$ ions, which are preferably present in the aqueous solution in a concentration of 0.05 mol/l to 2.0 mol/l $Sr^{2-}$. In this way, strontium compounds are formed in the layer created by plasmachemical treatment. This is advantageous because strontium carbonate in particular is hardly soluble in water and thus forms a layer component in the surface layer that has a particularly strong inhibiting effect on the degradation. Furthermore, the strontium carbonate present in the coating can manifest a drug-like effect against cerebral sclerosis, particularly in cranial applications.

In a preferred embodiment of the method according to the invention, additionally one or more ions selected from the group consisting of phosphates, carbonates, hydroxides and silicates are present in the aqueous solution that is used for the plasmachemical treatment.

If the aqueous solution for the plasmachemical treatment comprises phosphate ions, phosphates of the body material, in addition to the oxides and hydroxides, are formed in the layer created by plasmachemical treatment, which ensure better biocompatibility of the implant material, in particular of the coating. The phosphate ions originate from the addition of potassium dihydrogen phosphate and/or dipotassium hydrogen phosphate and/or potassium phosphate and/or sodium dihydrogen phosphate (dihydrate) and/or heptahydrate and/or dodecahydrate to the aqueous electrolyte. The preferred concentration range is between 5 g/l and 200 g/l of the added compound in the aqueous solution. A particularly preferred concentration is between 50 g/l and 100 g/l potassium dihydrogen phosphate.

In order to maintain a constant pH in the electrolyte (aqueous solution), a buffer, preferably potassium dihydrogen phosphate and/or sodium dihydrogen phosphate, is present in the aqueous solution.

In another preferred embodiment, the implant body is treated electrochemically, preferably electrochemically polished, before applying the metallic coating or before the plasmachemical treatment. This removes impurities from the surface of the implant body so that the application of the metallic coating or the plasmachemical treatment is carried out on a defined surface. The absence of surface contamination, which would otherwise result in poor adhesion of the layer created by plasmachemical treatment, is important. Electropolishing results in low-contamination cover layers due to major material removal effects (depth effect).

The plasmachemical treatment of the implant body is preferably carried out in that a pulsed voltage, preferably a positive voltage, is applied to the body, the amplitude of the voltage (peak voltage) exceeding at least approximately 90V during the predominant part of the treatment, particularly preferably exceeding at least approximately 100V, and preferably increasing in the course of the treatment. The voltage curve corresponds to the curve referred to above as the mixed or pulsed voltage.

Due to these high pulsed voltages having a pulse length of preferably no more than approximately 50 microseconds, particularly preferably approximately 5 microseconds, plasmas are generated on the surface of the implant body, lasting for a few microseconds and leading to the reaction of the metallic material of the implant body with the electrolyte. Between the voltage pulses, pauses of preferably approximately 1000 microseconds are provided. The energy to be applied in the form of voltage pulses is at least approximately 0.5 Ws for an implant surface of 100 mm$^2$. For implant surfaces having different sizes, the minimum energy changes proportionally to the area of the surface.

The plasmachemical process is preferably carried out with a current density of at least is approximately 3 mA/cm$^2$, preferably at least approximately 5 mA/cm$^2$.

In a further, particularly preferred embodiment, the plasmachemical treatment of an implant having a metallic coating, which contains titanium and preferably contains no aluminum, is followed by an after-treatment of the body of the implant in an aqueous, strongly basic sodium hydroxide solution in order to generate a pore base layer, wherein the after-treatment is carried out by applying ultrasound and/or injecting argon and/or nitrogen. The pH range is preferably between 11 and approximately 13.8, depending on the NaOH concentration. The temperature of the after-treatment solution preferably ranges between room temperature and 70° C. The preferred residence time of the implant body in the sodium hydroxide solution is between 5 seconds and 180 seconds.

Due to the after-treatment, the pore bottoms, which are critical with respect to the corrosion resistance and/or permeability, of the layer created by the plasmachemical coating are sealed, so that the pore base layer is present substantially in the pore bottoms. Only the pore bottoms, and not the entire pores, are closed by the after-treatment, so the positive effect of the surface roughened by the plasmachemical treatment and the associated high adhesion for polymer cover layers are preserved. In this way, an increased corrosion resistance of the implant is achieved, which results in degradation and loss of integrity within a time window of 3 to 12 months, which is of interest for many treatments.

The sealing effect of the pore bottom, which is achieved in this preferred embodiment according to the invention and based on the formation of hydroxides (titanium hydroxides, for example), also brings about a very advantageous crack-stopping mechanism. This mechanism occurs due to the difference in the mechanical consistency of the material of the porous cover layer on the one hand, and the material of the sealed pore bottom on the other hand. It is based on the high capacity of the pores to absorb cracking energy.

Microcracks occur, for example, at the moment of dilation of stents or other implants, when they are stressed beyond the plasticization capacity thereof in microscopic regions and result in uncontrolled and therefore undesirable degradation of the base material of the implant body. The cracks occurring in the preferred exemplary embodiment in the layer created by the plasmachemical treatment, largely comprising X-ray amorphous oxides, hydroxides and/or phosphates of the base material, are stopped in the pore bottoms. This is based on the geometry of the pore, which is static per se and thus accumulates cracking energy, as well as on the hydroxide (titanium hydroxide, for example) which is disposed in the pore bottom and is viscous in comparison with the remaining layer matrix. The hydroxide layer at the pore bottom is advantageously reinforced by the after-treatment according to the invention, so that the crack-stopping mechanism described here functions particularly effectively. In this way, high damage tolerance is achieved under mechanical stress, so that the degradation takes place more uniformly. The third layer, which is formed substantially at the bottom of the pores of the layer created by the plasmachemical treatment, generally has a thickness of a few 10 nm.

Another advantage of the claimed combination of the layer created by the plasmachemical treatment and the pore base layer is that no formation of bubbles occurs, and therefore no loss of lumen occurs with advanced degradation due to the semi-permeability of the layer composite, and/or the formation of bubbles is reduced.

In a further preferred embodiment, a further layer (hereinafter referred to as the fourth layer), preferably comprising a polymer, particularly preferably comprising at least one polymer of the group consisting of parylene and PLA (polylactide), in particular PLLA (poly-L-lactide), is applied to the layer created by plasmachemical treatment and/or to the pore base layer, after the plasmachemical treatment or after the after-treatment described above. Preferred layer thicknesses of the fourth layer range between approximately 0.5 and approximately 10 μm. Due to such a layer combination, the degradation time of the implant can be further increased significantly. The high gap penetration capacity of parylene has an advantageous effect, so that parylene penetrates deeper into the pores of the layer created by plasmachemical treatment and/or of the pore base layer down to the bottoms of the pores. The permeation properties for water, chloride-containing solutions and hydrogen, which are characteristic of PLA and parylene, in particular parylene N, in conjunction with the subjacent surface, which has been created by plasmachemical treatment and is optionally sealed at the bottoms of the pores, ensure a controllable degradation behavior of the implant. This behavior is also characterized by slow, uniform progression of the corrosion over the cross-section of the implant. Furthermore, the fourth layer makes an additional contribution to preventing or impairing the propagation of cracks under mechanical stress and prevents partial detachment of layers. It is particularly preferred if the fourth layer is made of parylene N or PLLA L210.

Parylene here denotes completely linear, partially crystalline, non-crosslinked aromatic polymers. The various polymers have different properties and can be divided into four basic types, namely parylene C, parylene D, parylene N and parylene F. Parylene N is preferred for use as the fourth layer in the layer composite according to the invention.

The layer created by plasmachemical treatment and/or the pore base layer disposed beneath the fourth layer result in a high adhesion capacity of the fourth layer because of the porous structure thereof, so that a primer treatment, which would otherwise be necessary beforehand, becomes redundant.

The above object is also achieved by an implant that can be obtained by a method according to the invention as described above. Such an implant has the advantages described above in connection with the production method according to the invention. According to the invention, after step b) the metallic coating has a first layer thickness, and after step c) it has a second layer thickness of the layer created by plasmachemical treatment which is greater than the first layer thickness. This is due to the fact that the layer created by plasmachemical treatment results from a transformation of the metallic coating and a transformation of the subjacent, near-surface layer of the implant body by the plasma.

The layer created by way of the plasmachemical treatment preferably has a thickness (second layer thickness) of at least 0.3 μm, preferably at least 1 μm.

As already described above, the layer created by plasmachemical treatment has pores, wherein a hydroxide of the metallic material or of the metallic materials of the implant body and/or of the metallic coating is preferably formed as the pore base layer at the bottoms of the pores, in particular during a treatment of the implant in a sodium hydroxide solution as described above.

The layer created by plasmachemical treatment preferably comprises at least one compound selected from the group consisting of
 alloys made of the material of the implant body and the material of the metallic layer, in particular alloys made of magnesium and one of the elements of aluminum and titanium, and
 phosphates, hydroxides and oxides of the material of the implant body and of the material of the metallic layer, in particular phosphates, hydroxides and oxides of magnesium, titanium and aluminum.

A composition gradient is observed from the surface of the implant downward to the transition of the layer created by plasmachemical treatment into the material of the implant body.

The advantage of aluminum and/or titanium as a constituent of the metallic coating, and hence as a constituent of the layer created by plasmachemical treatment, is that these materials can be oxidized with considerably lower energy expenditure during the plasmachemical treatment than other metallic materials. This means that the depth effect of the plasmachemical treatment, which is to say the ability of the plasma to reach the material of the implant body and to oxidize it, and to establish a bonded connection with the metal of the metallic coating, is associated with lower energy input. This is, above all, due to the considerably lower melting point of aluminum (660° C.) or titanium (approximately 1670° C.)

in comparison with metals such as tantalum (approximately 3000° C.) or niobium (approximately 2470° C.).

A further advantage of the implant according to the invention is that, as a result of the surface functionalization, the body of the implant does not come immediately in contact with a metal surface during the initial phase of the residence time of the implant in the body. This reduces the risk of inflammations, and at least during the first few hours of the residence time of the implant in the body, the endothelial cells have no or only little contact with metal ions.

In addition, the deformability of the implant, for example during dilation, is improved. This is due to the fact that a gradient of the modulus of elasticity exists from the outer surface of the implant according to the invention, this being the outer surface of the layer created by plasmachemical treatment, inward. This significantly reduces the mechanical stresses between the implant surface and the neutral phase on the inside of the component.

The methods according to the invention will be described hereinafter based on examples and figures. All characteristics illustrated and/or described form the subject matter of the invention, regardless of how they are combined in the claims or dependent claims.

DETAILED DESCRIPTION

Example 1

Figure 1:
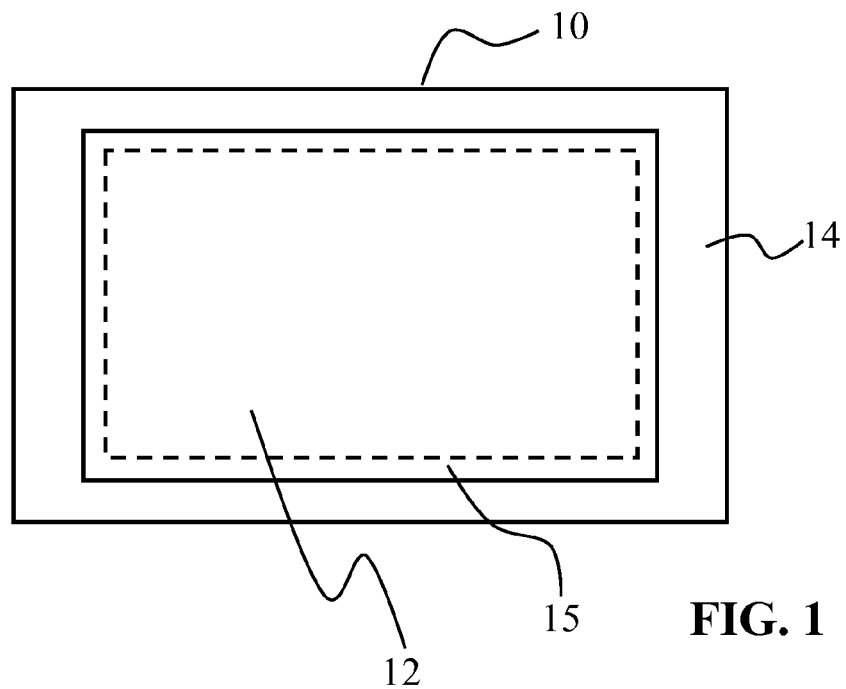
FIG. 1 depicting a cross-section of a strut of an implant (stent) according to the invention after step b) of the method according to the invention, FIG. 2 depicting a cross-section of a strut of the implant according to the invention of FIG. 1 after step c) of the method according to the invention, and FIG. 3 depicting a cross-section of a strut of the implant according to the invention of FIG. 2, comprising an additional layer containing a polymer.

A cross-sectional view of a strut 10 of a stent, which is made of a hollow-cylindrical mesh, for example, is shown in FIG. 1. The strut 10 has a rectangular cross-section. Cross-sections having different shapes (round, oval, triangular etc.) are also conceivable.

A stent body 12, made of the magnesium alloy WE43, is first coated, by way of an ionic fluid, with a coating 14 comprising aluminum and having a first layer thickness of approximately 1 µm to 2 µm.

The stent body 12 is coated by way of an ionic fluid as follows: The electrolyte is an ionic fluid and comprises 1-butyl-1-methylpyrrolidinium-bis(trifluoromethylsulfonyl)amide ([$Py_{1,4}$]TFSA). This fluid form a two-phase mixture with $AlCl_3$ in the concentration range of 1.6 to 2.5 mol $L^{-1}$. The coating is carried out at a temperature of the ionic fluid of 100° C. The coating time is approximately 2 to 4 hours. The potentiostatic polarization is −0.9 V versus Al/$A^{III}$.

Figure 2:
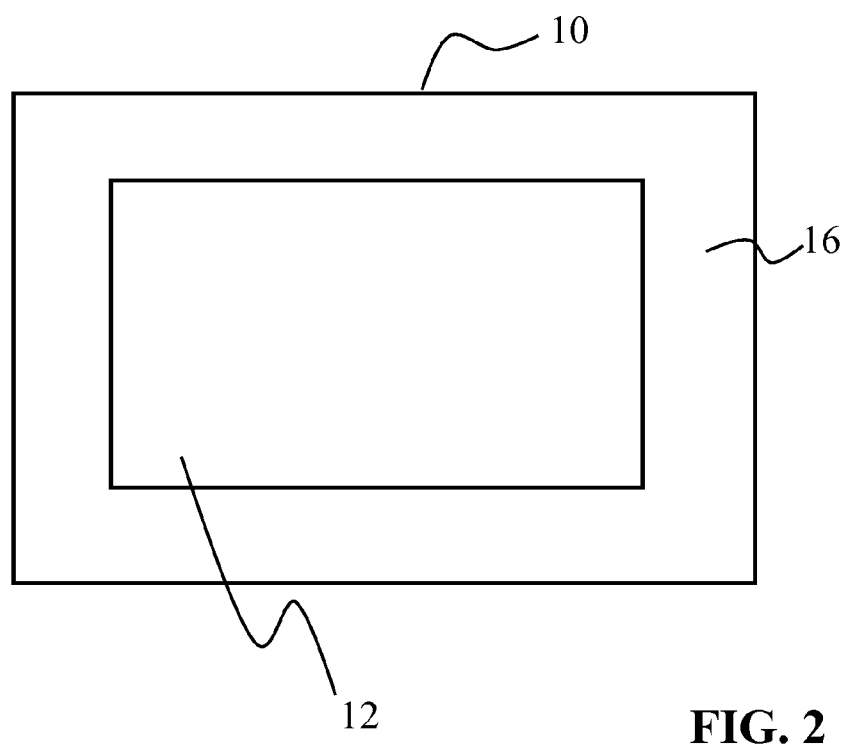

Then, plasmachemical oxidation is carried out in an aqueous, phosphate-containing electrolyte. This results in a layer 16 which has the properties described above and is approximately 3 µm thick and created by plasmachemical treatment. The resulting cross-section of the stent strut is illustrated in FIG. 2.

In FIG. 1, the dotted line marks the region 15 of the stent body 12 which is located beneath the coating 14 and which is ionized together with the coating 14 during the plasmachemical oxidation. After the plasmachemical oxidation has ended, the transformed region 15 of the stent body 12, together with the transformed coating 14, forms the layer 16 created by plasmachemical treatment (see FIG. 2).

The plasmachemical coating method, comprises the following steps, for example:

Contacting the stent body 12 with a wire made of titanium,

Immersing the stent body 12 provided with the coating 14 into the aqueous electrolyte having the following composition (aqueous base):

20 g/l ammonium carbonate (($NH_4$)$_2CO_3 \cdot H_2O$)
    20 g/l potassium dihydrogen phosphate ($KH_2PO_4$)
    20 g/l sodium carbonate ($Na_2CO_3$)
    100 ml/l aqueous ammonia solution (25%)
    100 ml/l ethylene diamine ($C_2H_8N_2$)

Applying a steadily increasing pulsed direct current from 0V upward, wherein the curve of the voltage corresponds to the curve referred to above as the mixed or pulsed voltage. The end-point voltage (maximum value of the peak voltage) of 450 V is reached after approximately 1 minute.

The average voltage is approximately 300 V because the lower cell voltage range is passed very quickly.

Removing the stent body 12, which has now been provided with the layer 16 created by plasmachemical treatment, from the electrolyte and decontacting it in air, and drying the stent as described above.

Figure 3:
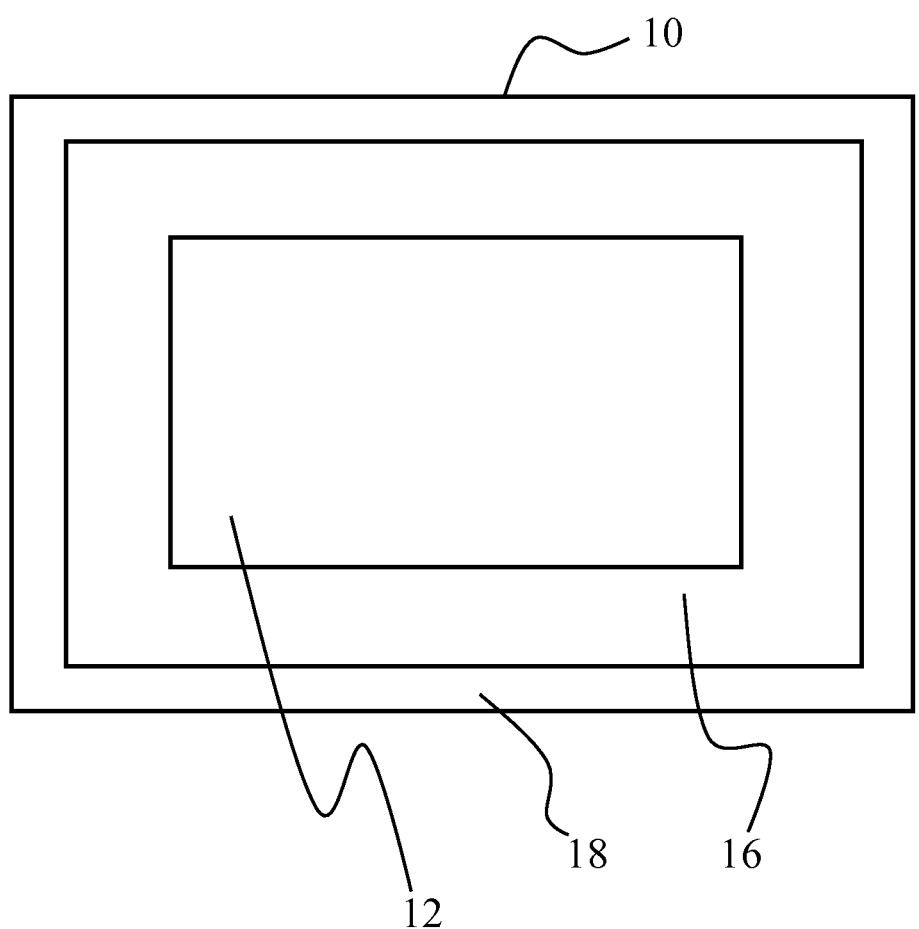

The stent produced in this way can then be sprayed with a degradable polymer, such as PLLA L210, which may optionally be loaded with a pharmaceutically active substance, by using known methods. A cross-section of a strut having a polymer coating is illustrated in FIG. 3. The polymer layer is denoted with the reference numeral 18 and has a layer thickness of approximately 2 µm.

Example 2

The stent body 12 made of a magnesium alloy WE43 is coated by way of ionic fluid with a 1 µm thick layer made of titanium (instead of aluminum used in Example 1). Then, plasmachemical oxidation is carried out in an aqueous, phosphate-containing electrolyte. This results in a layer having the properties described above, which is approximately 3 µm thick and produced by plasmachemical treatment. It also contains, for example, titanium dioxide ($TiO_2$), which gives the stent higher biocompatibility than a stent that is made of the same alloy, but only electropolished.

Over Example 1, only the deposition protocol from the ionic fluid changes as a result of the use of titanium instead of aluminum. The electrolyte is an ionic fluid and comprises 1-methyl-3-butylimidazolium-bis(trifluoromethylsulfone) ([BMIm]BTA).

Titanium(IV) chloride dissolves very easily in this fluid. For the deposition, a concentration of 0.24 mol·$1^{-1}$ $TiCl_4$ is adjusted. The coating is carried out at room temperature. The coating time is approximately 4 to 6 hours. The potentiostatic polarization is −1.9 V versus ferrocene when using counter and reference electrodes made of platinum.

The service life of a stent that has been coated according to Example 1 or Example 2 (without polymer coating) is higher by a factor of 1.5 compared to the reference. This means that a stent, which was stored for 42 days in artificial plasma (pH=7.4) buffered with HEPES (2-(4-(2-hydroxyethyl)-1-piperazinyl)-ethane sulfonic acid), still has approximately 70% of the original collapse pressure. The composition of the plasma is as follows (aqueous solution):

| Compound present in the plasma | Concentration [g/l] |
|---|---|
| NaCl | 6.8 |
| $CaCl_2$ | 0.2 |
| KCl | 0.4 |
| $MgSO_4 \cdot 7H_2O$ | 0.205 |
| $NaHCO_3$ | 2.2 |
| $Na_2HPO_4$ | 0.126 |
| $NaH_2PO_4 \cdot H_2O$ | 0.03 |

Uncoated reference stents comprising the magnesium alloy WE43, without additional coating, at this point only exhibit collapse pressure values of no more than 40% of the starting value of untreated stents. Metallographic analyses additionally verify that the remaining metallic residual cross-section (measured in the cross-section polish) of a strut of a stent produced according to the invention after this period is still approximately 60% of the starting cross-section prior to the treatment. Uncoated reference stents, in contrast, only have 30% to 40% of the metallic residual cross-section after this period.

In vivo analyses conducted on stents produced according to the above Example 1 or 2 showed that no inflammatory effects occur upon contact with endogenous cells. This applies to all coating variants (with aluminum, with titanium, and in each case also with an additional polymer cover layer). No differences were found between the solution according to the invention and uncoated implants made of the magnesium alloy WE 43.

During the use of the solution according to the invention from Example 1 as an orthopedic implant (animal tests on rabbits), a lower hydrogen development was observed compared to an uncoated magnesium implant. This can be attributed to the delayed degradation process.

Histological analyses showed that, in addition to the delayed degradation, the implants coated according to Example 1 or 2, which are either provided with a polymer coating or have no polymer coating, also have a more uniform decrease in the metallic residual fraction over the entire dimension of the implant than uncoated implants made of the magnesium alloy WE 43, and thus the supporting action is preserved for a longer time. This simplifies the calculation of the decrease in the ability to tolerate mechanical stresses as the implantation time progresses and makes the calculation more reliable.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE NUMERALS

10 Strut of the stent
12 Body of the stent
14 Metallic coating
15 Volume region of the stent body 12 which is located beneath the metallic coating 14 and which is ionized together with the metallic coating 14 during the plasmachemical oxidation
16 Layer created by plasmachemical treatment
18 Polymer layer

What is claimed is:

1. A method for producing an implant in a form of an intraluminal endoprosthesis, having a body, wherein the body comprises magnesium or a magnesium alloy, comprising the following steps:
   a) preparing the implant body,
   b) applying a metallic coating onto at least a portion of the body surface, the primary constituent of the coating being at least one element selected from titanium or aluminum,
   c) performing a plasmachemical treatment of the portion of the body surface provided with the coating in an aqueous solution comprising strontium$^{2-}$ ($Sr^{2-}$) ions in a concentration of 0.05 mol/l to 2.0 mol/l $Sr^{2-}$ by applying a mixed voltage generating the plasma to the body of the implant, wherein the mixed voltage has sufficient energy to temporarily ionize both the metallic coating and a subjacent region of the implant body to transform the subjacent region and metallic surface into a layer bonded to the implant body.

2. The method according to claim 1, characterized in that a first layer thickness of the metallic coating after completing step b) is from approximately 0.1 μm to approximately 3 μm.

3. The method according to claim 1, characterized in that the metallic coating is applied by way of an ionic fluid, by way of a physical vapor deposition (PVD) method, or by way of a chemical vapor deposition (CVD) method.

4. The method according to claim 1, characterized in that the implant is rinsed in a solvent, preferably distilled $H_2O$, after step c) and is then dried at a temperature of at least about 80° C.

5. The method according to claim 4, characterized in that the implant is dried in a circulating air oven at a temperature of at least approximately 100° C.

6. The method according to claim 1, characterized in that the aqueous solution additionally comprises one or more ions selected from the group consisting of phosphates, carbonates and silicates.

7. The method according to claim 6, further comprising a buffer of potassium hydrogen phosphate and/or sodium dihydrogen phosphate.

8. The method according to claim 1, characterized in that the plasmachemical treatment of the body surface is carried out in that a pulsed voltage is applied to the body, the peak voltage of which in the predominant part of the treatment period exceeds at least approximately 90V and increases in the course of the treatment to approximately 450V, wherein the current density during the plasmachemical treatment is at least approximately 3 $mA/cm^2$.

9. The method according to claim 8, characterized in that the predominant part of the treatment period exceeds at least approximately 100V and the current density during the plasmachemical treatment is at least approximately 5 $mA/cm^2$.

10. The method according to claim 1, characterized in that after step c) an after-treatment of the implant body is carried out in an aqueous, strongly basic sodium hydroxide solution, which has a pH value between approximately 11 and 13.8, in order to create a pore base layer, wherein the after-treatment is conducted by applying ultrasound and/or injecting argon and/or nitrogen.

11. The method according to claim 1, characterized in that a further layer comprising a polymer is applied to the layer created by plasmachemical treatment.

12. The method according to claim 11, wherein the polymer is selected from the group consisting of poly(p-xylylene) polymer, polylactide (PLA), and poly-L-lactide (PLLA).

* * * * *